United States Patent
Schulein et al.

(10) Patent No.: US 6,268,197 B1
(45) Date of Patent: Jul. 31, 2001

(54) XYLOGLUCAN-SPECIFIC ALKALINE XYLOGLUCANASE FROM BACILLUS

(75) Inventors: Martin Schulein, Copenhagen; Helle Outtrup, Ballerup; Per Lina Jorgensen, Copenhagen; Mads Eskelund Bjornvad, Frederiksberg, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/110,959

(22) Filed: Jul. 7, 1998

Related U.S. Application Data

(60) Provisional application No. 60/063,694, filed on Oct. 28, 1997, and provisional application No. 60/054,039, filed on Jul. 28, 1997.

(30) Foreign Application Priority Data

| Jul. 7, 1997 | (DK) | .................................................... 0822/97 |
| Oct. 24, 1997 | (DK) | .................................................... 1213/97 |

(51) Int. Cl.[7] ............................. C12N 9/42; D06N 16/00; C11D 7/42; C11D 3/386
(52) U.S. Cl. ......................... 435/209; 435/263; 510/320; 510/392; 510/530
(58) Field of Search .................................. 435/209, 263; 510/320, 392, 530

(56) References Cited

FOREIGN PATENT DOCUMENTS

| 5068549 | 3/1993 | (JP) . |
| WO 93/17101 | 9/1993 | (WO) . |
| WO 94/14953 | 7/1994 | (WO) . |
| WO 96/07743 | 3/1996 | (WO) . |
| WO 96/34092 | 10/1996 | (WO) . |

OTHER PUBLICATIONS

Rejon–Palomers et al., Symbiosis sida, vol. 21, No. 3, pp. 249–261 (1996).
Maclachlan et al., Aust. J. Plant Physiol., vol., 19, pp. 137–146 (1992).
Vincken et al., Carbohydrate Research, vol. 298, pp. 299–310 (1997).
de Silva et al., "Molecular Characterization of a Xyloglucan–Specific Endo–(1→4)–β–d–Glucanase (Xyloglucan Endo–Transglycosylase) from Nasturtium Seeds", Plant J., 3(5), 701–11, in Chem Abs. AN 119:244271, 1993.*
Matsumoto et al., "Purification of Xyloglucanase from Auxin–treated Pea Stems", Wood Res., 83, 21–22, in Chem Abs. AN 126:273990, 1996.*
MacLachlan et al., "Endo–1,4–β–Glucanase, Xyloglucanase, and Xyloglucan Endo–Transglycosylase Activities Versus Potential Substrates In Ripening Tomatoes", Plant Physiol., 105(3), 965–74, Jul. 1994.*
Vincken et al., "The Effect of Xyloglucans on the Degradation of Cell–Wall–Embedded Cellulose by the Combined Action of Cellobiohydrolase and Endoglucanases from Trichoderma Viride", Plant Physiol., 104(1), 99–107, Jan. 1994.*
Vincken et al., "Fungal and Plant Xyloglucanases May Act in Concert During Liquefaction of Apples", J. Sci. Food Agric., 73(4), 407–416, Apr. 1997.*
Edwards et al., "Purification and Properties of a Novel Xyloglucan–Specific Endo–(1→4)–β–D–glucanase from Germinated Nasturtium Seeds (Tropaeolum majus L.)", J. Biol. Chem., 261(20), 9489–9494, Jul. 1986.*

\* cited by examiner

*Primary Examiner*—Jon P. Weber
(74) *Attorney, Agent, or Firm*—Elias J. Lambiris, Esq.; Jason I. Garbell, Esq.

(57) ABSTRACT

A xyloglucanase having a relative xyloglucanase activity of at least 50% at pH 7 and either no or an insignificant cellulolytic activity is obtainable e.g. from a strain of Bacillus. A xyloglucanase comprising an amino acid sequence as shown in positions 30–261 of SEQ ID NO:2 or homologues may be derived from eg *Bacillus licheniformis*, ATCC 14580, and may be encoded by polynucleotide molecules comprising a nucleotide sequence as shown in SEQ ID NO:1 from nucleotide 88 to nucleotide 783; and a xyloglucanase comprising an amino acid sequence as shown in positions 1–537 of SEQ ID NO:4 or homologues may be derived from eg *B. agaradhaerens*, NCIMB 40482, and may be encoded by polynucleotide molecules comprising a nucleotide sequence as shown in SEQ ID NO:3 from nucleotide 1 to nucleotide 1611. The xyloglucanases are useful e.g. in cleaning compositions and for treatment of cellulosic fibres.

12 Claims, No Drawings

SEQUENCE LISTING

<160> NUMBER OF SEQ ID NOS: 14

<210> SEQ ID NO: 1
<211> LENGTH: 786
<212> TYPE: DNA
<213> ORGANISM: Bacillus licheniformis ATCC 14580

<400> SEQUENCE: 1

```
gtgaaaaaca accatttgct aaaatccatt ctgctatggg gtgccgtatg catcatagtg      60
ctggcagggc cgctctcagc atttgccgct tcgtcatcaa acccgtcgga taaattgtat     120
tttaaaaaca aaaatactac catattcaac aatgtatggg gagccgacca ggtcagcggc     180
tggtggcaga ccatttatca taatagtgat tcagatatgg gctgggtgtg gaattggccg     240
agcaatacaa gcacggtaaa agcttatccg tcgatcgtca gcggctggca ttggactgaa     300
ggctatactg ccggaagcgg cttcccgacg cgattgtcag atcaaaaaaa catcaacacg     360
aaagtcagct attcgatcag cgcaaacggc acatacaatg ccgcatatga catttggctc     420
cacaatacaa acaaggcgag ctgggattcg gctccaaccg atgagattat gatctggctc     480
aataacacaa acgccggacc tgccggttcc tatgtcgaaa ctgtatcgat tggcgggcac     540
agttggaaag tatataaagg ctatattgat gctggaggcg gcaaagggtg gaacgtgttt     600
tcatttatca gaacagcaaa cacccaaagt gcgaacctga atattcggga tttcacgaat     660
tatcttgccg actccaaaca gtggctttcc aaaacaaagt atgtcagcag tgtggaattc     720
ggtactgaag ttttcggagg cacaggacaa attaatattt ccaattggga cgtaacggtc     780
cgctga                                                                786
```

<210> SEQ ID NO: 2
<211> LENGTH: 261
<212> TYPE: PRT
<213> ORGANISM: Bacillus licheniformis ATCC 14580

<400> SEQUENCE: 2

```
Val Lys Asn Asn His Leu Leu Lys Ser Ile Leu Leu Trp Gly Ala Val
1               5                  10                  15

Cys Ile Ile Val Leu Ala Gly Pro Leu Ser Ala Phe Ala Ala Ser Ser
            20                  25                  30

Ser Asn Pro Ser Asp Lys Leu Tyr Phe Lys Asn Lys Tyr Tyr Ile
        35                  40                  45

Phe Asn Asn Val Trp Gly Ala Asp Gln Val Ser Gly Trp Trp Gln Thr
    50                  55                  60

Ile Tyr His Asn Ser Asp Ser Asp Met Gly Trp Val Trp Asn Trp Pro
65                  70                  75                  80

Ser Asn Thr Ser Thr Val Lys Ala Tyr Pro Ser Ile Val Ser Gly Trp
                85                  90                  95

His Trp Thr Glu Gly Tyr Thr Ala Gly Ser Gly Phe Pro Thr Arg Leu
            100                 105                 110

Ser Asp Gln Lys Asn Ile Asn Thr Lys Val Ser Tyr Ser Ile Ser Ala
        115                 120                 125

Asn Gly Thr Tyr Asn Ala Ala Tyr Asp Ile Trp Leu His Asn Thr Asn
    130                 135                 140

Lys Ala Ser Trp Asp Ser Ala Pro Thr Asp Glu Ile Met Ile Trp Leu
145                 150                 155                 160

Asn Asn Thr Asn Ala Gly Pro Ala Gly Ser Tyr Val Glu Thr Val Ser
```

```
                    165                 170                 175
Ile Gly Gly His Ser Trp Lys Val Tyr Lys Gly Tyr Ile Asp Ala Gly
                180                 185                 190
Gly Gly Lys Gly Trp Asn Val Phe Ser Phe Ile Arg Thr Ala Asn Thr
            195                 200                 205
Gln Ser Ala Asn Leu Asn Ile Arg Asp Phe Thr Asn Tyr Leu Ala Asp
        210                 215                 220
Ser Lys Gln Trp Leu Ser Lys Thr Lys Tyr Val Ser Ser Val Glu Phe
225                 230                 235                 240
Gly Thr Glu Val Phe Gly Gly Thr Gly Gln Ile Asn Ile Ser Asn Trp
                245                 250                 255
Asp Val Thr Val Arg
            260

<210> SEQ ID NO: 3
<211> LENGTH: 1614
<212> TYPE: DNA
<213> ORGANISM: Bacillus agaradhaerens NCIMB 40482

<400> SEQUENCE: 3
gaagatgtca cttcgtcaca gttggatatt cactcctatg tagctgacat gcagcctggc      60
tggaatttag gaaatacgtt tgacgctgtt ggagatgatg aaacagcgtg ggggaatcct     120
cgtgtaacaa gagagttaat aaaaacgatt gctgatgaag gtataaaag cattcgtatc     180
ccagtgacat ggcaaaatca atgggtggt ctccagatt atacgataaa tgaagattat     240
atcaatcggg tggagcaagc gatagattgg gcgttggagg aagacttata tgtgatgtta     300
aatgtgcatc atgactcatg gctgtggatg tatgatatgg aacataacta tgatgaggtc     360
atggcaagat atacagctat ttgggaacaa ttgtcggaaa aattcaaaag ccactcccat     420
aagttgatgt tgagagtgt caatgagcct aggtttacgc aggagtgggg agagattcaa     480
gaaaatcatc atgcttactt agaagattta ataagacgt tctattatat tgtcagagag     540
tcaggaggca ataatgtgga gcgccctta gtattgccta cgatagaaac agccacgtct     600
caggatttac tagatcgctt gtatcaaaca atggaagact ggatgatcc ttatttaatt     660
gccacggtgc attattatgg cttctggcca tttagtgtca atatagcagg gtacactcat     720
tttgaacagg aaacacaaca agatattata gacacctttg accgtgttca taacacattt     780
acagcgcgtg tgtcccagt tgtattaggc gaattcggtt tgttaggctt tgacaaaagt     840
acggatgtga ttcagcaagg ggagaaatta agtttttg agtttctcat ccatcatctc     900
aatgaacgtg atataaccca tatgttatgg gataacggcc agcattttaa tcgagaaact     960
tatgcatggt atgatcaaga atttcatgac atattaaaag cgagttggga ggggcgttct    1020
gctacagcag agtctaattt gattcatgtg aaggacggaa agccaattag agatcaagat    1080
atacagcttt acttaaacgg aaatgagcta acagccttac aggcagggga ggaatcgctt    1140
gttctaggag aggattatga actagcagga ggcgtattaa cgctaaaagc ggacaccctc    1200
acaagactaa ttaccccctgg tcaattagga accaatgcag tcatcacagc acaatttaat    1260
tctggagcag actggcgttt tcaattacag aatgtggacg tgccaacggt cgaaaataca    1320
gatggctcaa catggcattt tgcgatccct acccatttta atggtgatag tcttgcgacg    1380
atggaagctg tttatgcaaa cggagaatat gctgggccgc aagattggac gtcatttaaa    1440
gaatttggcg aggcgttttc tcctaattac gccacagggg aaattattat atcagaagcc    1500
ttctttaacg cggtacggga tgatgatatc catttaacat ttcattttg gagcggagag    1560
```

```
acgtggaat ataccttacg taaaaatggc aattatgttc aaggtagacg gtaa        1614
```

<210> SEQ ID NO: 4
<211> LENGTH: 537
<212> TYPE: PRT
<213> ORGANISM: Bacillus agaradhaerens NCIMB 40482

<400> SEQUENCE: 4

```
Glu Asp Val Thr Ser Ser Gln Leu Asp Ile His Ser Tyr Val Ala Asp
  1               5                  10                  15

Met Gln Pro Gly Trp Asn Leu Gly Asn Thr Phe Asp Ala Val Gly Asp
             20                  25                  30

Asp Glu Thr Ala Trp Gly Asn Pro Arg Val Thr Arg Glu Leu Ile Lys
         35                  40                  45

Thr Ile Ala Asp Glu Gly Tyr Lys Ser Ile Arg Ile Pro Val Thr Trp
     50                  55                  60

Gln Asn Gln Met Gly Gly Ser Pro Asp Tyr Thr Ile Asn Glu Asp Tyr
 65                  70                  75                  80

Ile Asn Arg Val Glu Gln Ala Ile Asp Trp Ala Leu Glu Glu Asp Leu
                 85                  90                  95

Tyr Val Met Leu Asn Val His His Asp Ser Trp Leu Trp Met Tyr Asp
            100                 105                 110

Met Glu His Asn Tyr Asp Glu Val Met Ala Arg Tyr Thr Ala Ile Trp
        115                 120                 125

Glu Gln Leu Ser Glu Lys Phe Lys Ser His Ser His Lys Leu Met Phe
    130                 135                 140

Glu Ser Val Asn Glu Pro Arg Phe Thr Gln Glu Trp Gly Glu Ile Gln
145                 150                 155                 160

Glu Asn His His Ala Tyr Leu Glu Asp Leu Asn Lys Thr Phe Tyr Tyr
                165                 170                 175

Ile Val Arg Glu Ser Gly Gly Asn Asn Val Glu Arg Pro Leu Val Leu
            180                 185                 190

Pro Thr Ile Glu Thr Ala Thr Ser Gln Asp Leu Leu Asp Arg Leu Tyr
        195                 200                 205

Gln Thr Met Glu Asp Leu Asp Asp Pro Tyr Leu Ile Ala Thr Val His
    210                 215                 220

Tyr Tyr Gly Phe Trp Pro Phe Ser Val Asn Ile Ala Gly Tyr Thr His
225                 230                 235                 240

Phe Glu Gln Glu Thr Gln Gln Asp Ile Ile Asp Thr Phe Asp Arg Val
                245                 250                 255

His Asn Thr Phe Thr Ala Arg Gly Val Pro Val Val Leu Gly Glu Phe
            260                 265                 270

Gly Leu Leu Gly Phe Asp Lys Ser Thr Asp Val Ile Gln Gln Gly Glu
        275                 280                 285

Lys Leu Lys Phe Phe Glu Phe Leu Ile His His Leu Asn Glu Arg Asp
    290                 295                 300

Ile Thr His Met Leu Trp Asp Asn Gly Gln His Phe Asn Arg Glu Thr
305                 310                 315                 320

Tyr Ala Trp Tyr Asp Gln Glu Phe His Asp Ile Leu Lys Ala Ser Trp
                325                 330                 335

Glu Gly Arg Ser Ala Thr Ala Glu Ser Asn Leu Ile His Val Lys Asp
            340                 345                 350

Gly Lys Pro Ile Arg Asp Gln Asp Ile Gln Leu Tyr Leu Asn Gly Asn
        355                 360                 365
```

```
Glu Leu Thr Ala Leu Gln Ala Gly Glu Glu Ser Leu Val Leu Gly Glu
         370                 375                 380

Asp Tyr Glu Leu Ala Gly Gly Val Leu Thr Leu Lys Ala Asp Thr Leu
385                 390                 395                 400

Thr Arg Leu Ile Thr Pro Gly Gln Leu Gly Thr Asn Ala Val Ile Thr
             405                 410                 415

Ala Gln Phe Asn Ser Gly Ala Asp Trp Arg Phe Gln Leu Gln Asn Val
         420                 425                 430

Asp Val Pro Thr Val Glu Asn Thr Asp Gly Ser Thr Trp His Phe Ala
         435                 440                 445

Ile Pro Thr His Phe Asn Gly Asp Ser Leu Ala Thr Met Glu Ala Val
         450                 455                 460

Tyr Ala Asn Gly Glu Tyr Ala Gly Pro Gln Asp Trp Thr Ser Phe Lys
465                 470                 475                 480

Glu Phe Gly Glu Ala Phe Ser Pro Asn Tyr Ala Thr Gly Glu Ile Ile
             485                 490                 495

Ile Ser Glu Ala Phe Phe Asn Ala Val Arg Asp Asp Ile His Leu
         500                 505                 510

Thr Phe His Phe Trp Ser Gly Glu Thr Val Glu Tyr Thr Leu Arg Lys
         515                 520                 525

Asn Gly Asn Tyr Val Gln Gly Arg Arg
         530                 535

<210> SEQ ID NO: 5
<211> LENGTH: 42
<212> TYPE: DNA
<213> ORGANISM: Bacillus sp.

<400> SEQUENCE: 5
gtcgccgggg cggccgctat caattggtaa ctgtatctca gc                42

<210> SEQ ID NO: 6
<211> LENGTH: 64
<212> TYPE: DNA
<213> ORGANISM: Bacillus sp.

<400> SEQUENCE: 6
gtcgcccggg agctctgatc aggtaccaag cttgtcgacc tgcagaatga ggcagcaaga   60
agat                                                               64

<210> SEQ ID NO: 7
<211> LENGTH: 61
<212> TYPE: DNA
<213> ORGANISM: Bacillus sp.

<400> SEQUENCE: 7
gtcggcggcc gctgatcacg taccaagctt gtcgacctgc agaatgaggc agcaagaaga   60
t                                                                  61

<210> SEQ ID NO: 8
<211> LENGTH: 35
<212> TYPE: DNA
<213> ORGANISM: Bacillus sp.

<400> SEQUENCE: 8
gtcggagctc tatcaattgg taactgtatc tcagc                              35
```

-continued

```
<210> SEQ ID NO: 9
<211> LENGTH: 35
<212> TYPE: DNA
<213> ORGANISM: Bacillus sp.

<400> SEQUENCE: 9
aacagctgat cacgactgat cttttagctt ggcac                           35

<210> SEQ ID NO: 10
<211> LENGTH: 37
<212> TYPE: DNA
<213> ORGANISM: Bacillus sp.

<400> SEQUENCE: 10
aactgcagcc gcggcacatc ataatgggac aaatggg                         37

<210> SEQ ID NO: 11
<211> LENGTH: 44
<212> TYPE: DNA
<213> ORGANISM: Bacillus sp.

<400> SEQUENCE: 11
gcctcattct gcagcagcgg cggcttcgtc atcaaacccg tcgg                 44

<210> SEQ ID NO: 12
<211> LENGTH: 45
<212> TYPE: DNA
<213> ORGANISM: Bacillus sp.

<400> SEQUENCE: 12
gctgcatcgg catcgcggcc gcggcaatac gtaaggatgg tatcg                45

<210> SEQ ID NO: 13
<211> LENGTH: 39
<212> TYPE: DNA
<213> ORGANISM: Bacillus sp.

<400> SEQUENCE: 13
cattctgcag ccgcggcaga agatgtcact tcgtcacag                       39

<210> SEQ ID NO: 14
<211> LENGTH: 41
<212> TYPE: DNA
<213> ORGANISM: Bacillus sp.

<400> SEQUENCE: 14
gttgagaaaa gcggccgcca cttctaaagt tctaaagcac g                    41
```

XYLOGLUCAN-SPECIFIC ALKALINE XYLOGLUCANASE FROM BACILLUS

CROSS-REFERENCE TO RELATED APPLICATIONS

This application claims priority under 35 U.S.C. 119 of United States Provisional application nos. 60/054,039 and 60/063,694 filed Jul. 28, 1997 and Oct. 28, 1997, respectively, and of Danish application nos. 0822/97 and 1213/97 filed Jul. 7, 1997 and Oct. 24, 1997, respectively, the contents of which are fully incorporated herein by reference.

The present invention relates to alkaline xyloglucanases, i.e. enzymes exhibiting xyloglucanase activity as their major enzymatic activity in the neutral and alkaline pH ranges; to a method of producing such enzymes; and to methods for using such enzymes in the textile, detergent and cellulose fiber processing industries.

BACKGROUND OF THE INVENTION

Xyloglucan is a major structural polysaccharide in the primary (growing) cell wall of plants. Structurally, xyloglucans consists of a cellulose-like beta-1,4-linked glucose backbone which is frequently substituted with various side chains. The xyloglucans of most dicotyledonous plants, some monocotyledons and gymnosperms are highly branched polysaccharides in which approx. 75% of the glucose residues in the backbone bear a glycosyl side chain at 0–6. The glycosyl residue that is directly attached to the branched glucose residue is invariably alpha-D-xylose. Up to 50% of the side chains in the xyloglucans contain more than one residue due to the presence of beta-D-galactose or alpha-L-fucose-(1–2)-beta-D-galactose moieties at 0–2 of the xylose residues (C. Ohsumi and T. Hayashi (1994) Plant and Cell Physiology 35:963–967; G. J. McDougall and S. C. Fry (1994) Journal of Plant Physiology 143:591–595; J. L. Acebes et al. (1993) Phytochemistry 33:1343–1345). On acid hydrolysis, the xyloglucan extracted from cotton fibers yielded glucose, xylose, galactose and fucose in the ratio of 50:29:12:7 (Hayashi et al., 1988).

Xyloglucans produced by solanaceous plants are unusual in that typical only 40% of the beta-1,4-linked glucose residues bear a glycosyl side chain at 0–6. Furthermore, up to 60% of the xylose residues are substituted at 0–2 with alfa-L-arabinose residues and some solanaceous plants, such as potato, also have xyloglucans with beta-D-galactose substituents at 0–2 of some of the xylose residues (York et al (1996)).

Xyloglucan is believed to function in the primary wall of plants by crosslinking cellulose-microfibrils, forming a cellulose-xyloglucan network. This network is considered necessary for the structural integrity of primary cell-walls (Carpita et al., 1993). Another important function of xyloglucan is to act as a repository for xyloglucan subunit oligosaccharides that are physiologically active regulators of plant cell growth. Xyloglucan subunits may also modulate the action of a xyloglucan endotransglycosylase (XET), a cell-wall associated enzyme that has been hypothesized to play a role in the elongation of plant cell walls. Therefore xyloglucan might play an important role in wall loosening and consequently cell expansion (Fry et al., 1992).

The seeds of many dicotyledonous species contain xyloglucan as the major polysaccharide storage reserve. This type of xyloglucan, which is localized in massive thickenings on the inside of the seed cotyledon cell wall, is composed mainly of glucose, xylose and galactose (Rose et al., 1996).

Seeds of the tamarind tree *Tamarindus indica* became a commercial source of gum in 1943 when the gum was found useful as a paper and textile size. Sizing of jute and cotton with tamarind xyloglucan has been extensively practiced in Asia owing to the low cost of the gum and to its excellent properties. Food applications of tamarind xyloglucan include use in confections, jams and jellies and as a stabilizer in ice cream and mayonnaise (Whistler et al., 1993).

Xyloglucanase activity is not included in the classification of enzymes provided by the Enzyme Nomenclature (1992). Hitherto, this enzymatic activity has simply been classified as glucanase activity and has often been believed to be identical to cellulolytic activity (EC 3.2.1.4), i.e. activity against β-1,4-glycosidic linkages in cellulose or cellulose derivative substrates, or at least to be a side activity in enzymes having cellulolytic activity. However, a true xyloglucanase is a true xyloglucan specific enzyme capable of catalyzing the solubilisation of xyloglucan to xyloglucan oligosaccharides but which does not exhibit substantial cellulolytic activity, e.g. activity against the conventionally used cellulose-like substrates CMC (carboxymethylcellulose), HE cellulose and Avicel (microcrystalline cellulose). A xyloglucanase cleaves the beta-1,4-glycosidic linkages in the backbone of xyloglucan.

Xyloglucanase activity is described by Vincken et al. (1997) who characterizes three different endoglucanases from *Trichoderma viride* (similar to *T. reesei*) which all have high activity against cellulose or CMC and show that the EndoI (which is indeed belonging to family 5 of glycosyl hydrolases, see Henrissat, B. et al. (1991, 1993)) has essentially no (i.e. very little) activity against xyloglucan, and that EndoV (belonging to the family 7 of glycosyl hydrolases) and EndoIV (belonging to the family 12 of glycosyl hydrolases) both have activity against xyloglucan and CMC, respectively, of the same order of magnitude.

International patent publication WO 97/13862 describes two cellulases from *Aspergillus niger* strain N400 as described in EP-A 0 463 706. The sequence of lac12 can be ascribed to family 12, and the sequence of lac64 is determined as belonging to family 5 by comparison with known homologous cellulases in the EMBL data base. Both enzyme have cellulase and β-glucanase activity. They have the highest activity against barley β-glucan, and they both show good CMC activity and some xyloglucanase activity. Both enzyme has pH optima at 3.5 on CMC and 5.5 on barley β-glucan.

International Patent Publication WO 94/14953 discloses a xyloglucanase (EG II) cloned from the fungus *Aspergillus aculeatus* and expressed in the fungus *Aspergillus oryzae* which has high xyloglucanase activity and very little cellulase activity. This EG II enzyme which shows xyloglucanase activity in the pH range 2.5–6 and optimum activity at pH 3–4 also belongs to family 12 of glycosyl hydrolases.

In summary, up till now xyloglucanase activity has only been found in fungal enzymes belonging to the families 7 and 12 of glycosyl hydrolases and exhibiting this activity in the acidic to near neutral pH range.

However, many important processes, either industrial or using industrially produced agents, are operating at an alkaline pH. Thus, it is an object of the present invention to provide a true xyloglucanase enzyme with a high xyloglucanase activity at an alkaline pH and essentially no activity on cellulose or cellulose derivatives.

SUMMARY OF THE INVENTION

The inventors have now found enzymes having substantial xyloglucanase activity in the alkaline range, such enzymes having either no or an insignificant cellulolytic activity.

Accordingly, the present invention relates to an enzyme preparation comprising a xyloglucanase having a relative xyloglucanase activity of at least 50% at pH 7 or a pH above 7, and preferably a minor or no activity on cellulose or cellulose derivative substrates, e.g. having a ratio of maximum xyloglucanase activity to maximum activity on CMC or Avicel of at least 2:1.

The inventors have also succeeded in cloning and expressing a xyloglucanase, ie the invention relates in further aspects to a xyloglucanase which is (a) a polypeptide produced by *Bacillus agaradhaerens*, N CIMB 40482, or (b) a polypeptide comprising an amino acid sequence as shown in positions 1–537 SEQ ID NO:4, or (c) an analogue of the polypeptide defined in (a) or (b) which is at least 70% homologous with said polypeptide, or is derived from said polypeptide by substitution, deletion or addition of one or several amino acids, or is immunologically reactive with a polyclonal antibody raised against said polypeptide in purified form; and to a xyloglucanase which is (a) a polypeptide produced by *Bacillus licheniformis*, ATCC 14580, or (b) a polypeptide comprising an amino acid sequence as shown in positions 30–261 of SEQ ID NO:2, or (c) an analogue of the polypeptide defined in (a) or (b) which is at least 70% homologous with said polypeptide, or is derived from said polypeptide by substitution, deletion or addition of one or several amino acids, or is immunologically reactive with a polyclonal antibody raised against said polypeptide in purified form; and to an isolated polynucleotide molecule encoding a polypeptide having xyloglucanase activity selected from (a) polynucleotide molecules comprising a nucleotide sequence as shown in SEQ ID NO:1 from nucleotide 88 to nucleotide 783; (b) polynucleotide molecules that encode a polypeptide that is at least 70% identical to the amino acid sequence of SEQ ID NO:2 from amino acid residue 30 to amino acid residue 261; and (c) degenerate nucleotide sequences of (a) or (b); and to an isolated polynucleotide molecule encoding a polypeptide having xyloglucanase activity selected from the group consisting of:

(a) polynucleotide molecules comprising a nucleotide sequence as shown in SEQ ID NO:3 from nucleotide 1 to nucleotide 1611;

(b) polynucleotide molecules that encode a polypeptide that is at least 70% identical to the amino acid sequence of SEQ ID NO:4 from amino acid residue 1 to amino acid residue 537; and (c) degenerate nucleotide sequences of (a) or (b).

In further aspects, the invention provides an expression vector comprising a DNA segment which is eg a polynucleotide molecule of the invention; a cell comprising the DNA segment or the expression vector; and a method of producing an enzyme exhibiting xyoglucanase activity, which method comprises culturing the cell under conditions permitting the production of the enzyme, and recovering the enzyme from the culture.

In yet another aspect the invention provides an isolated enzyme exhibiting xyloglucanase activity, characterized in (i) being free from homologous impurities and (ii) the enzyme is produced by the method described above.

The novel enzyme of the present invention is useful for the treatment of cellulosic material, especially cellulose-containing fiber, yarn, woven or non-woven fabric. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising an enzyme having substantial xyloglucanase activity in the alkaline range; and to use of the enzyme of the invention for the treatment of cellulose-containing fibers, yarn, woven or non-woven fabric.

The present invention has now made it possible to use a truly enzymatic scouring process in the preparation of cellulosic material e.g. for proper response in subsequent dyeing operations. Further, it is contemplated that detergent compositions comprising the novel enzyme are capable of removing or bleaching certain soils or stains present on laundry, especially soils and spots resulting from xyloglucan-containing food, plants, and the like. It is also contemplated that treatment with detergent compositions comprising the novel enzyme can prevent binding of certain soils to the xyloglucan left on the cellulosic material.

DETAILED DESCRIPTION OF THE INVENTION

Cellulases are found in more than 10 different families of glycosyl hydrolases. Some of the cellulases also exhibit xyloglucanase activity. Today, such cellulases have been found among those classified in the families 5, 7 and 12. The substrate specificity is, however, not directly correlated with the family: within a family the main enzymatic activity can be cellulase or mannanase (family 5), or lichinase, $\beta$-1,3-glucanase or xyloglucantransferase activity (family 16). The only enzyme hitherto disclosed as having activity against xyloglucan as the major or main enzymatic activity is the *Aspergillus aculeatus* EG II disclosed in WO 94/14953. As mentioned above, this activity has not yet an entry in the official Enzyme Nomenclature.

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant xyloglucanase, but which microorganism simultaneously produces other enzymes, e.g. xyloglucanases, proteases, or cellulases, being naturally occurring fermentation products of the microorganism, i.e. the enzyme complex conventionally produced by the corresponding naturally occurring microorganism.

In a preferred embodiment, the xyloglucanase has a relative activity at pH 7 of at least 50%, preferably at least 75%, more preferably at least 80%, especially at least 90%, compared to the activity at the optimal pH.

In another preferred embodiment, the xyloglucanase has a relative activity at pH 8 of at least 50%, preferably at least 60%, more preferably at least 75%, especially at least 90%, compared to the activity at the optimal pH.

In yet another preferred embodiment, the xyloglucanase has a relative activity at pH 9 of at least 10%, preferably at least 20%, more preferably at least 25%, compared to the activity at the optimal pH.

In yet another preferred embodiment, the xyloglucanase has a relative activity at pH 9.5 of at least 5%, preferably at least 10%, more preferably at least 15%, compared to the activity at the optimal pH.

In yet another preferred embodiment, the xyloglucanase has a relative activity at pH 10 of at least 5%, compared to the activity at the optimal pH.

In another preferred embodiment the xyloglucanase has a relative activity at a temperature of 50° C., preferably of at least 60%, preferably at least 70%, compared to the activity at the optimal temperature.

In yet another preferred embodiment, at a temperature of 60° C., the relative xyloglucanase activity is at least 40%, preferably at least 50%; at a temperature of 70° C., the relative xyloglucanase activity is at least 40%, preferably at least 45%, especially at least 50%.

In a preferred embodiment, the xyloglucanase has a minor or no activity on cellulose or cellulose derivative substrates. A conventional substrate for determining cellulase activity (endo-β1,4-glucanase activity, jf. EC 3.2.1.4) is carboxymethylcellulose (CMC). Another conventional substrate for determining cellulase or cellobiohydrolase activity (EC 3.2.1.91) is Avicel which is a micro-crystalline cellulose well known by the person skilled in the art. Preferably, the ratio of maximum xyloglucanase activity to maximum activity on either CMC or Avicel is at least 2:1, more preferably at least 3:1, more preferably at least 4:1, even more preferably at least 5:1, even more preferably at least 8:1, especially at least 10:1.

The xyloglucanase preparation of the invention may further comprise one or more enzymes selected from the group consisting of proteases, cellulases (endo-β1,4-glucanases), β-glucanases (endo-β1,3(4)-glucanases), lipases, cutinases, peroxidases, laccases, amylases, glucoamylases, pectinases, reductases, oxidases, phenoloxidases, ligninases, pullulanases, arabinanases, hemicellulases, mannanases, galactanases, xylanases, pectin acetyl esterases, rhamnogalacturonan acetyl esterases, polygalacturonases, rhamnogalacturonases, pectin lyases, pectate lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are monocomponent enzyme(s) which is/are mixed with the other enzyme(s) to form an enzyme preparation with the desired enzyme blend.

In another aspect, the present invention also relates to a method of producing the enzyme preparation of the invention, the method comprising culturing a microorganism capable of producing the xyloglucanase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the xyloglucanase enzyme. The growth medium may contain a conventional N-source such as peptone, yeast extract or casamino acids, a reduced amount of a conventional C-source such as dextrose or sucrose, and an inducer such as xyloglucan or composit plant substrates such as cereal brans (e.g. wheat bran or rice husk). The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

In the present context the term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

POLYNUCLEOTIDES

Within preferred embodiments of the invention an isolated polynucleotide of the invention will hybridize to similar sized regions of SEQ ID NO:1 or SEQ ID NO:3, or a sequence complementary thereto, under at least medium stringency conditions.

In particular polynucleotides of the invention will hybridize to a denatured double-stranded DNA probe comprising either the full sequence shown in SEQ ID NO:3 or the full sequence shown in positions 88–783 of SEQ ID NO:1 or any probe comprising a subsequence of SEQ ID NO:3 or SEQ ID NO:1 having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×10^9 cpm/µg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having endoglucanase activity of the invention are then identified and isolated by, for example, hybridization or PCR.

The present invention further provides counterpart polypeptides and polynucleotides from different bacterial strains (orthologs or paralogs). of particular interest are xyloglucanase polypeptides from gram-positive alkalophilic strains, including species of Bacillus.

Species homologues of a polypeptide with xyloglucanase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA sequence of the invention encoding an polypeptide having xyloglucanase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the xylooglucanase cloned from B. licheniformis, ATCC 14580, or from B. agaradhaerens, NCIMB 40482, expressed and purified as described in Materials and Methods and Examples 5, 6 and 7, or by an activity test relating to a polypeptide having xyloglucanase activity.

POLYPEPTIDES

The sequence of SEQ ID NO:4 and of amino acids nos. 30–261 of SEQ ID NO:2, respectively, is a mature xyloglucanase sequence of the catalytic active domain. The present invention also provides xyloglucanase polypeptides that are substantially homologous to the polypeptide of SEQ ID NO:2 or SEQ ID NO:4 and species homologs (paralogs or orthologs) thereof. The term "substantially homologous" is used herein to denote polypeptides having 75%, preferably at least 80%, more preferably at least 85%, and even more preferably at least 90%, sequence identity to the sequence shown in SEQ ID NO:4 or in amino acids nos. 30–261 of SEQ ID NO:2 or their orthologs or paralogs. Such polypeptides will more preferably be at least 95% identical, and most preferably 98% or more identical to the sequence shown in SEQ ID NO:4 or in amino acids nos. 30–261 of SEQ ID NO:2 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a polypeptide of the invention having xyloglucanase activity.

TABLE 1

Conservative amino acid substitutions

| | |
|---|---|
| Basic | arginine |
| | lysine |
| | histidine |
| Acidic | glutamic acid |
| | aspartic acid |
| Polar | glutamine |
| | asparagine |
| Hydrophobic | leucine |
| | isoleucine |
| | valine |
| Aromatic | phenylalanine |
| | tryptophan |
| | tyrosine |
| Small | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the xyloglucanase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e xyloglucanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to SEQ ID NO:4 or residues 30 to 261 of SEQ ID NO:2 and retain the xyloglucanase activity of the wild-type protein.

The xyloglucanase enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part the encoded enzyme, or a CBD from another origin may be introduced into the xyloglucanase thus creating an enzyme hybride. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I-X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or as without a linker, to a DNA sequence encoding the xyloglucanase and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of a polypeptide encoded by the polynucleotide molecule of the invention.

The Xyloglucan Substrate

In addition to the aforesaid about xyloglucan it should be noted that xyloglucan from tamarind seeds supplied by Megazyme, Australia has a complex branched structure with glucose, xylose, galactose and arabinose in the ratio of 45:36:16:3. Accordingly, it is strongly believed that an enzyme showing catalytic activity on this xyloglucan also has catalytic activity on other xyloglucan structures from different sources (angiosperms ot gymnosperms).

Use in the Detergent Industry

During washing and wearing, dyestuff from dyed fabrics or garment will conventionally bleed from the fabric which then looks faded and worn. Removal of surface fibers from the fabric will partly restore the original colours and looks of the fabric. By the term "colour clarification", as used herein, is meant the partly restoration of the initial colours of fabric or garment throughout multiple washing cycles.

The term "de-pilling" denotes removing of pills from the fabric surface.

The term "soaking liquor" denotes an aqueous liquor in which laundry may be immersed prior to being subjected to a conventional washing process. The soaking liquor may contain one or more ingredients conventionally used in a washing or laundering process.

The term "washing liquor" denotes an aqueous liquor in which laundry is subjected to a washing process, i.e. usually a combined chemical and mechanical action either manually or in a washing machine. Conventionally, the washing liquor is an aqueous solution of a powder or liquid detergent composition.

The term "rinsing liquor" denotes an aqueous liquor in which laundry is immersed and treated, conventionally immediately after being subjected to a washing process, in order to rinse the laundry, i.e. essentially remove the detergent solution from the laundry. The rinsing liquor may contain a fabric conditioning or softening composition.

The laundry subjected to the method of the present invention may be conventional washable laundry. Preferably, the major part of the laundry is sewn or unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, flax/linen, jute, cellulose acetate fibers, lyocell).

DETERGENT DISCLOSURE AND EXAMPLES

Surfactant System

The detergent compositions according to the present invention comprise a surfactant system, wherein the surfactant can be selected from nonionic and/or anionic and/or cationic and/or ampholytic and/or zwitterionic and/or semi-polar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ Co-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

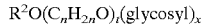
$R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, pre-ferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}E(1.0)M$), $C_{12}$–$C_{18}$ alkyl polyethoxylate (2.25) sulfate ($C_{12}$–$C_{18}(2.25)M$, and $C_{12}$–$C_{18}$ alkyl polyethoxylate (3.0) sulfate ($C_{12}$–$C_{18}E(3.0)M$), and $C_{12}$–$C_{18}$ alkyl polyethoxylate (4.0) sulfate ($C_{12}$–$C_{18}E(4.0)M$), wherein M is conveniently selected from sodium and potassium. Suitable anionic surfactants to be used are alkyl ester sulfonate surfactants including linear esters of $C_8$–$C_{20}$ carboxylic acids (i.e., fatty acids) which are sulfonated with gaseous SO₃ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

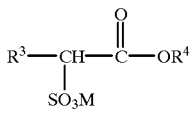

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

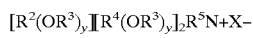

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$$R_1R_2R_3R_4N^+X^- \quad (i)$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) wherein $R_1$ is

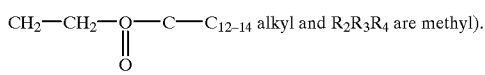

$CH_2$—$CH_2$—O—C—$C_{12-14}$ alkyl and $R_2R_3R_4$ are methyl).

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

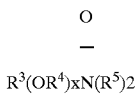

$R^3(OR^4)xN(R^5)2$ wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2, -ethane tetracarboxylates, 1,1,3,3-propane tetracarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan—cis, cis, cis-tetracarboxylates, 2,5-tetrahydro-furan-cis, discarboxylates, 2,2,5,5-tetrahydrofuran—tetracarboxylates, 1,2,3,4,5,6-hexane—hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include Na$_2$EDDS and Na$_4$EDDS. Examples of such preferred magnesium salts of EDDS include MgEDDS and Mg$_2$EDDS. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme(s) which provides cleaning performance and/or fabric care benefits.

Such enzymes include proteases, lipases, cutinases, amylases, cellulases, peroxidases, oxidases (e.g. laccases).

Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a *Pseudomonas* lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a *Bacillus lipase*, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase (a and/or b) suitable for use in alkaline solutions can be used. Suitable amylases include those of bacterial or fungal origin. Chemically or genetically modified mutants are included. Amylases include, for example, a-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307 which discloses fungal cellulases produced from *Humicola insolens*, in WO 96/34108 and WO 96/34092 which disclose bacterial alkalophilic cellulases (BCE 103) from Bacillus, and in WO 94/21801, U.S. Pat. No. 5,475,101 and U.S. Pat. No. 5,419,778 which disclose EG III cellulases from Trichoderma. Especially suitable cellulases are the cellulases having colour care benefits. Examples of such cellulases are cellulases described in European patent application No. 0 495 257. Commercially available cellulases include Celluzyme™ and Carezyme™ produced by a strain of *Humicola insolens* (Novo Nordisk A/S), KAC-500(B)™ (Kao Corporation), and Puradax™ (Genencor International).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases: Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and Wo 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching Agents

Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process.

Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", *Nature* 369, 1994, pp. 637–639.

Suds Suppressors

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/ silica mixture in combination with fumed nonporous silica such as Aerosil$^R$.

The suds suppressors described above are normally employed at levels of from 0.001% to 2% by weight of the composition, preferably from 0.01% to 1% by weight.

Other Components

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4,4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:21'-disulphonate, monosodium 4',4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2, 1,3-triazol-2-yl)-stilbene-2,2' disulphonate, di-sodium 4,4'bis( 2-anilino-4-(1-methyl-2-hydroxyethylamino)-s-triazin-6-ylamino)stilbene-2,2'disulphonate, sodium 2(stilbyl-4"-(naphtho-1',2':4,5)-1,2,3,—triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. No. 4,116,885 and 4,711,730 and EP 0 272 033. A particular preferred polymer in accordance with EP 0 272 033 has the formula:

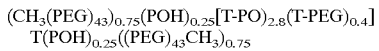

where PEG is —(OC$_2$H$_4$)0—, PO is (OC$_3$H$_6$O) and T is (pOOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening Agents

Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-transfer Inhibiting Agents

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention. In the detergent compositions, the abbreviated component identifications have the following meanings:

LAS: Sodium linear $C_{12}$ alkyl benzene sulphonate

TAS: Sodium tallow alkyl sulphate

XYAS: Sodium $C_{1X}$–$C_{1Y}$ alkyl sulfate

SS: Secondary soap surfactant of formula 2-butyl octanoic acid

25EY: A $C_{12}$–$C_{15}$ predominantly linear primary alcohol condensed with an average of Y moles of ethylene oxide 45EY: A $C_{14}$–$C_{15}$ predominantly linear primary alcohol condensed with an average of Y moles of ethylene oxide XYEZS: $C_{1X}$–$C_{1Y}$ sodium alkyl sulfate condensed with an average of Z moles of ethylene oxide per mole Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh CFAA: $C_{12}$–$C_{14}$ alkyl N-methyl glucamide TFAA: $C_{16}$–$C_{18}$ alkyl N-methyl glucamide Silicate: Amorphous Sodium Silicate ($SiO_2$:$Na_2O$ ratio= 2.0)

NaSKS-6: Crystalline layered silicate of formula d-$Na_2Si_2O_5$

Carbonate: Anhydrous sodium carbonate

Phosphate: Sodium tripolyphosphate

MA/AA: Copolymer of 1:4 maleic/acrylic acid, average molecular weight about 80,000

Polyacrylate: Polyacrylate homopolymer with an average molecular weight of 8,000 sold under the tradename PA30 by BASF GmbH Zeolite A: Hydrated Sodium Aluminosilicate of formula $Na_{12}(AlO_2SiO_2)_{12}.27H_2O$ having a primary particle size in the range from 1 to 10 micrometers Citrate: Tri-sodium citrate dihydrate Citric: Citric Acid Perborate: Anhydrous sodium perborate monohydrate bleach, empirical formula $NaBO_2.H_2O_2$ PB4: Anhydrous sodium perborate tetrahydrate Percarbonate: Anhydrous sodium percarbonate bleach of empirical formula $2Na_2CO_3.3H_2O_2$ TAED: Tetraacetyl ethylene diamine CMC: Sodium carboxymethyl cellulose DETPMP: Diethylene triamine penta (methylene phosphonic acid), marketed by Monsanto under the Tradename Dequest 2060

PVP: Polyvinylpyrrolidone polymer

EDDS: Ethylenediamine-N,N'-disuccinic acid, [S,S] isomer in the form of the sodium salt Suds Suppressor: 25% paraffin wax Mpt 50° C., 17% hydrophobic silica, 58% paraffin oil Granular Suds suppressor: 12% Silicone/silica, 18% stearyl alcohol, 70% starch in granular form Sulphate: Anhydrous sodium sulphate HMWPEO: High molecular weight polyethylene oxide TAE 25: Tallow alcohol ethoxylate (25)

DETERGENT EXAMPLE I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

DETERGENT EXAMPLE II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

DETERGENT EXAMPLE III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

DETERGENT EXAMPLE IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |

-continued

|  |  |  |
|---|---|---|
| Granular suds suppressor | 1.0 | 4.0 |
| CMC | 0.2 | 0.1 |
| Water/Minors | Up to 100% | |

DETERGENT EXAMPLE V

Heavy duty liquid fabric cleaning compositions in accordance with the invention may be prepared as follows:

|  | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water / Minors | Up to 100% | |

Use in the Textile and Cellulosic Fiber Processing Industries

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The preparation of the present invention is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are desizing (for woven goods), scouring and bleaching. A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme α-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

It is contemplated that the scouring step can be carried out using the xyloglucanase or xyloglucanase preparation of the present invention in combination with a few other enzyme activities at a temperature of about 50° C.–80° C. and a pH of about 7–11, thus substituting or supplementing the highly causticizing agents.

Competent cells were prepared and transformed as described by Yasbin et al. (1975).

Plasmids.

pSJ1678 (see WO 94/19454).

pMOL944. This plasmid is a pUB110 derivative essentially containing elements making the plasmid propagatable in *Bacillus subtilis*, kanamycin resistance gene and having a strong promoter and signal peptide cloned from the amyL gene of *B. licheniformis* ATCC 14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of ordinary genetic engineering and is briefly described in the following.

Construction of pMOL944:

The pUB110 plasmid (McKenzie, T. et al., 1986,) was digested with the unique restriction enzyme NciI. A PCR fragment amplified from the amyL promoter encoded on the plasmid pDN1981 (Jørgensen et al.,1990) was digested with NciI and inserted in the NciI digested pUB110 to give the plasmid pSJ2624.

The two PCR primers used have the following sequences:

```
#LWN5494 5'-GTCGCCGGGGCGGCCGCTATCAATTGGTAACTGTATCTCAGC-3'           SEQ ID NO:5

#LWN5495 5'-GTCGCCCGGGAGCTCTGATCAGGTACCAAGCTTGTCGACCTGCAGAATGAGGCAGCAAGAAGAT-3'   SEQ ID NO:6
```

MATERIALS AND METHODS

Strains:

*Bacillus licheniformis*, ATCC 14580, and *Bacillus agaradhaerens*, NCIMB 40482, respectively, comprises a DNA sequence of the invention encoding a xyloglucanase.

Other Strains:

*E. coli* strain: Cells of *E. coli* SJ2 (Diderichsen et al., 1990) were prepared for and transformed by electroporation using a Gene Pulser™ electroporator from BIO-RAD as described by the supplier.

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

```
#LWN5938 5'-GTCGGCGGCCGCTGATCACGTACCAAGCTTGTCGACCTGCAGAATGAGGCAGCAAGAAGAT-3'   SEQ ID NO:7

#LWN5939 5'-GTCGGAGCTCTATCAATTGGTAACTGTATCTCAGC-3'                            SEQ ID NO:8
```

*B. subtilis* PL1885. (Diderichsen et al., (1990)).

*B. subtilis* PL2306. This strain is the *B. subtilis* DN1885 with disrupted apr and npr genes (Diderichsen et al. (1990)) disrupted in the transcriptional unit of the known *Bacillus subtilis* cellulase gene, resulting in cellulase negative cells.

*B. subtilis* PL2316. This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321) disrupted in the transcriptional unit of the known *Bacillus subtilis* xylanase gene, resulting in xylanase negative cells. The disruptions were performed essentially as described in A. L. Sonenshein et al. (1993).

The plasmid pSJ2670 was digested with the restriction enzymes PstI and BclI and a PCR fragment amplified from a cloned DNA sequence encoding the alkaline amylase SP722 (International Patent Application published as WO95/26397 which is hereby incorporated by reference) was digested with PstI and BclI and inserted to give the plasmid pMOL944. The two primers used for PCR amplification have the following sequence:

```
#LWN7864 5'-AACAGCTGATCACGACTGATCTTTTAGCTTGGCAC-3'               SEQ ID NO:9

#LWN7901    5'-AACTGCAGCCGCGGCACATCATAATGGGACAAATGGG-3'         SEQ ID NO:10
```

The primer #LWN7901 inserts a SacII site in the plasmid.

Media:

TY (as described in Ausubel, F. M. et al. 1995).

LB agar (as described in Ausubel, F. M. et al, 1995).

LBPG is LB agar supplemented with 0.5% Glucose and 0.05 M potassium phosphate, pH 7.0

AZCL-xyloglucan is added to LBPG-agar to 0.5%. AZCL-xyloglucan is from Megazyme, Australia.

BPX media is described in EP 0 506 780 (WO 91/09129).

Medium A: Per flask: 30 g wheat bran, 45 ml of the following solution: 10 g rofec (Roquette 101-0441), 10 g $NH_4NO_3$ (Merck 1187), 10 g $KH_2PO_4$ (Merck 4873), 40 g Solcafloc (Dicacel availabe from Dicalite-Europe-Nord, 9000 Gent, Belgium), 0.75 g $MgSO_4.7H_2O$ (Merck 5886), 15 g $CaCO_3$, tap water to 1000 ml, pH adjusted to 6.5. Autoclave for 40 min at 121° C.

Medium B: 30 g soyabean meal, 15 g maltodex 01 (Roquette 101-7845), 5 g peptone (Difco 0118), 0.2 ml pluronic (PE-6100, 101-3068), deionized water up to 1000 ml. 100 ml in 500 ml Erlenmeyer flask with 2 baffles. Autoclave at 121° C. for 40 min.

Medium C: 15 g wheat bran, 5 g dextrose, 6.7 g Bacto Yeast Nitrogen Base, deionized water up to 1000 ml. 100 ml in 500 ml Erlenmeyer flask with 2 baffles. Autoclave at 121° C. for 40 min.

Medium D: 20% sucrose, 5% soy flakes and 1% sodium phosphate.

Medium E: 5 g Yeast Extract, 10 g Tryptone, 3 g $(NH_4)_2SO_4$, 3 g $K_2HPO_4$, 2 g $KH_2PO_4$, 1 g CMC, 10 g maltodextrin, 30 g wheat bran, deionized water up to 1000 ml, pH adjusted to 7.0. 100 ml in 500 ml Erlenmeyer flask with 2 baffles. Autoclave at 121° C. for 40 min.

Fermentation Procedure:

The fungal strains were grown in shake flasks under the following growth conditions:

| Media | A, B or C (see list of media) |
|---|---|
| Temperature | 26° C. |
| RPM | A, stationary |
|  | B and C, 125–200 |
| Incubation time | A, 6–30 days |
|  | B and C, 2–21 days |

Bacteria were grown in shake flasks containing medium D or E at 30° C. with 250 rpm shaking for 3–4 days.

Xyloglucanase Assay (XGU):

The xyloglucanase activity is measured using AZCL-xyloglucan from Megazyme, Australia, as substrate.

A solution of 0.2% of the blue substrate is suspended in a 0.1 M phosphate buffer pH 7.5 under stirring. The solution is distributed under stirring to 1.5 ml Eppendorf tubes (0.75 ml to each), 50 µl enzyme solution is added and they are incubated in an Eppendorp Thermomixer model 5436 for 20 min. at 40° C. with a mixing of 1200 rpm. After incubation the coloured solution is separated from the solid by 4 min. centrifugation at 14,000 rpm and the absorbance of the supernatant is measured at 600 nm.

One XGU units is defined as the amount of enzyme resulting in an absorbance of 0.24 in a 1 cm cuvette at 600 nm.

Isoelectric Focusing:

Isoelectric focusing was carried out in precast Ampholine PAG plates pH 3.5–9.5 (Pharmacia, Sweden) according to the manufacturer's instructions. The samples were applied in duplicate and after electrophoresis the gel was divided into two. An overlay containing 1% agarose and 0.4% AZCL xyloglucan in water was poured onto one half of the gel, a similar overlay containing AZCL HE cellulose was poured onto the other half. Incubation at 30° C. for 2–16 hours. Enzyme activity was identified by blue zones.

General Molecular Biology Methods:

DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

The following examples illustrate the invention.

EXAMPLE 1

Screening for Microorganisms Producing Alkaline Xyloglucanase

The microorganisms to be screened were grown in a liquid culture as described in the Materials and Methods section. After centrifugation the culture supernatants were tested for xyloglucanase and cellulase activity. The following assays were used: agarose plates containing 1% agarose in 0.08 M Britton-Robinson buffer pH 7 or pH 9, and 0.2% AZCL xyloglucan and 0.2% AZCL HE cellulose, respectively, 10 ml samples were applied into d=4 mm holes in the agarose plates, incubation at 30° C. for 2–16 hours. Enzyme activity was identified by blue halos.

Culture broths with good activity on AZCL xyloglucan and no or low activity on AZCL HE cellulose were further tested by isoelectric focusing (IEF) as described in the Materials and Methods section. The microorganisms listed in the Materials and Methods section were found to produce an enzyme with activity on AZCL xyloglucan which by IEF was separable from activity on AZCL HE cellulose. When screening for xyloglucanase activity also cellulase activity was found, and it was determined whether both activities derives from the same enzyme. This was done by separation of the enzymes by IEF isoelctric focusing which separates the protein according to the charge or pI. After this separation the different enzymatic activities was again identified using overlayer techniques. The sample was run at two parallel wells: one stained for xyloglucanase and another for AZCL HE-cellulose. If the same lane has both activities it is a cellulase, if only one lane has xyloglucanase and no cellulase activity it is a xyloglucanase which can be further characterized either by purification or by cloning.

EXAMPLE 2

Production of a *Bacillus licheniformis* Xyloglucanase (XG)

This example illustrates a method for producing xyloglucanase from *Bacillus licheniformis*.

*Bacillus licheniformis*, ATCC 14580, was grown in shake flasks using the substrate PS 1 (20% sucrose and 5% soy flakes and 1% sodium phosphate) at 30° C. with 250 rpm shaking for 4 days. The culture broth (total 10 litres) was adjusted to pH 7.5 with NaOH, followed by treatment with 50 ml of a cationic flocculation agent under stirring at room temperature and subsequently 470 ml of a 0.1% solution of an anionic flocculation agent. The flocculated material was separated by centrifugation using a Sorval RC 3B 10.000 rpm for 30 min. The supernatant was clarified using a Whatman glass filter number F. A total of 9 litres was obtained with an activity of 10 XGU per ml.

The liquid was concentrated to 1.5 litres on a filtron with a cut off at 10 kDa.

Bacitracin cross linked to Sepharose was used for affinity column chromatography for removal of the proteases. Then the not bound material was adjusted to pH 5.0 using acetic acid and applied to a SP-Sepharose column adjusted with 20 mM sodium acetate buffer pH 5.0. The XG activity was eluted from the column by using a 0.5 M NaCl gradient. The fractions containing XG activity was pooled and concentrated on an Amicon cell with a GR 81 polysulfon membrane with a cut off at 8 kDa.

The concentrated solution containing 363 XGU per ml was applied to size chromatography using a Superdex 200 column equilibrated with a buffer of 0.1 M sodium acetate pH 6.0. The pure XG 1 eluted with an apparent molecular weight of 26 kDa and gave a single band in SDS-PAGE of 26 kDa. The specific activity was determined to 221 XGU per A.280.

EXAMPLE 3

Characterisation of a *Bacillus licheniformis* Xyloglucanase

The amino acid sequence of the enzyme produced as described in Example 2 was obtained after SDS-PAGE and electroblotting of the 26 kDa protein. The amino acid sequence is listed in the appended SEQ ID No:2.

This amino acid shows highest homology with glycosyl hydrolases from Family 12 which at present are classified as endo-beta-1,4-glucanases (EC 3.2.1.4): 65% homology with the family 12 *Erwinia carotovora* β-1,4-glucan glucanohydrolase (celS—P16630 Swissprot).

Accordingly, the present invention further relates to an enzyme which has the amino acid sequence listed in SEQ ID NO:2 or has an amino acid sequence which is at least 70%, preferably at least 75%, more preferably at least 80%, more preferably at least 85%, even more preferably at least 90%, especially at least 95%, homologous therewith.

The obtained *Bacillus licheniformis* xyloglucanse enzyme was analysed using Megazyme AZCL xyloglucan for xyloglucanase activity determination and AZCL HE cellulose for endoglucanase activity determination. The relative release of blue colour was 40 times higher on the xyloglucan substrate compared with the HE cellulose using the same amount of purified enzyme.

The same result was found for the acidic Aspergillus aculeatus xyloglucanase enzyme (EG II) described in the patent application WO 94/14953 which also showed 2% relative activity against HE cellulose.

Temperature Optimum

The AZCL xyloglucan from Megazyme was also used for determination of temperature optimum. The activity was measured at different temperatures after incubation with the xyloglucanase of Example 2 for 20 minutes and the release of blue colour was determined at 600 nm. The major part of the colour was released at 60° C., but still 50% relative activity was obtained at 70° C.

pH Activity Profile

For obtaining a realistic pH activity profile, the activity determinations were carried out using buffers having a pKa value within 1.0 of the actual pH. The following buffer systems were used: pH 4–5.5 sodium acetate, pH 6 Mes buffer (Sigma), pH 6.5–7.5 Mops buffer (Sigma), pH 8–8.5 Barbiturate, pH 9–10.5 Glycine.

The pH was measured after incubation in a parallel handled tube. Incubation 20 min. at 40° C. Final substrate concentration 1.33 gram xyloglucan per l. This is the $K_M$ (see below for steady state at pH 7.5). The activity was determined after measurement of the formation of reducing ends as described for steady state kinetic.

| pH | % relative activity |
|------|---------------------|
| 4.13 | 7 |
| 4.59 | 32 |
| 5.05 | 83 |
| 5.54 | 100 |
| 6.00 | 97 |
| 6.49 | 84 |
| 6.99 | 96 |
| 7.52 | 90 |
| 7.99 | 61 |
| 8.49 | 45 |
| 9.02 | 27 |
| 9.41 | 14 |
| 9.90 | 5 |

EXAMPLE 4

Comparison Example: Steady State Kinetics on Soluble Xyloglucan and CMC

A method for determination of activity against xyloglucan has been developed.

The substrate is xyloglucan (amyloid) from tamarind seeds (the substrate is commercially available from Megazyme). Buffer 0.1 M sodium phosphate pH 7.5.

The substrate is prepared as a stock solution containing 5 gram per l in buffer. After mixing it is heated using a magnetic stirrer until a clear solution is obtained. The solution is then cooled to 40° C. and kept in a temperature controlled water bath at 40° C.

The diluted enzyme solution of 0.5 ml is preheated for 10 min. and mixed with 1.0 ml substrate and incubated for 20 min.

The formation of reducing sugars is determined by using p-hydroxy-benzoic-acid-hydrazide (PHBAH) modified from Lever (1972) using 5 gram of potassium sodium tartrate in addition to 1.5 gram of PHBAH. Glucose is used as reference for determination of the reducing groups.

The apparent catalytic properties of 2 known cellulases (endo-beta-1,4-glucanases) on xyloglucan from tamarind seeds was measured:

a. EG I from *Humicola insolens* (classified as belonging to family 7 of glycosyl hydrolases) disclosed in WO 95/24471.

b. EG III from Trichoderma (classified as belonging to family 12 of glycosyl hydrolases) disclosed in U.S. Pat. No. 5,475,101.

All the enzymes were purified to high homogeneity giving a single band in SDS-PAGE and the molar extinction coefficient was used for calculation of the enzyme concentration. The determination was based on different concentrations of the substrate from 0.25 to 3.3 gram per litre. The kinetic determination was according to the computer program Grafit and assuming Michelis Menten kinetic.

Results

Enzyme of the invention: *Bacillus licheniformis* Xyloglucanase 1 with a molecular weight (MW) of 26 kDa. Based on a molar absorbance of 78,000, determined by amino acid analysis, the $k_{cat}$ was 16.5 per sec (std. error 0.6) on xyloglucan at pH 7.5, Km 1.1 g/l (std. error 0.1). Using CMC as substrate the $k_{cat}$ was impossible to measure but below 3 per sec. The ratio of maximum xyloglucanase activity to maximum activity on CMC is at least 5:1.

a. Comparison EG I, alkaline cellulase from *Humicola insolens*, MW 50 kDa, molar extinction coefficient of 66310.

A $k_{cat}$ of 19 per sec (std. error 0.7) on xyloglucan at pH 7.5, $K_m$ 0.7 g/l (std. error 0.08). On CMC the $k_{cat}$ is 86 per sec (std. error 5). The ratio of maximum xyloglucanase activity to maximum activity on CMC is 2:9.

b. Comparison EG III, acid cellulase from Trichoderma, MW 24 kDa, molar extinction coefficient of 71930. A $k_{cat}$ of 16 per sec (std. error 1.7) on xyloglucan at pH 7.5, $K_m$ 0.5 g/l (std. error 0.15). On CMC the $k_{cat}$ is 18 per sec (Std. error 0.6). The ratio of maximum xyloglucanase activity to maximum activity on CMC is 8:9.

EXAMPLE 5

Cloning and Expression of the *Bacillus licheniformis* Xyloglucanase Gene

Genomic DNA Preparation:

Strain *Bacillus licheniformis*, ATCC 14580, was propagated in liquid TY medium. After 16 hours incubation at 30° C. and 300 rpm, the cells were harvested, and genomic DNA isolated by the method described by Pitcher et al., (1989).

Genomic Library Construction:

Genomic DNA was partially digested with restriction enzyme Sau3A, and size-fractionated by electrophoresis on a 0.7% agarose gel. Fragments between 2 and 10 kb in size was isolated by electrophoresis onto DEAE-cellulose paper (Dretzen et al., (1981)).

Isolated DNA fragments were ligated to BamHI digested pSJ1678 plasmid DNA, and the ligation mixture was used to transform *E. coli* SJ2.

Identification of Positive Clones:

A DNA library in *E. coli*, constructed as described above, was screened on LB agar plates containing 0.5% AZCL-xyloglucan (Megazyme) and 9 μg/ml Chloramphenicol and incubated overnight at 37° C. Clones expressing hydrolysing activity appeared with blue diffusion halos. Positive clones were plated on LB agar plates containing 0.5% AZCL-xyloglucan (Megazyme). The plasmids of this clones were isolated by Qiagen plasmid spin preps on 1 ml of overnight culture broth (cells incubated at 37° C. in TY with 9 μg/ml Chloramphenicol and shaking at 250 rpm). One of these clones (PL2949) was further characterized by DNA sequencing of the cloned Sau3A DNA fragment.

The DNA was characterised by DNA sequencing using the Taq deoxy-terminal cycle sequencing kit (Perkin-Elmer, USA), fluorescent labelled terminators and appropriate oligonucleotides as primers.

Analysis of the sequence data was performed according to Devereux et al. (1984). The sequence encoding the mature protein is shown in SEQ ID NO:1 (signal plus mature; the mature part corresponding to positions 88–783. The derived protein sequence is shown in SEQ ID NO:2, the mature protein corresponding to positions 30–261 og SEQ ID NO:2.

Subcloning and Expression of the Xyloglucanase Gene From *B. licheniformis* in *B. subtilis*:

The xyloglucanase encoding DNA sequence of the invention was PCR amplified using the PCR primer set consisting of these two oligonucleotides:

Xyloglu .upper.PstI

5'-GCCTCATT<u>CTGCAG</u>CAGCGGCGGCTTCGTCATC AAACCCGTCGG-3' SEQ ID NO:11

Xyloglu .lower.NotI

5'-GCTGCATCGGCATC<u>GCGGCCGC</u>GGCAATACGTA AGGATGGTATCG-3' SEQ ID NO:12

Restriction sites PstI and NotII are underlined.

Chromosomal DNA isolated from *B. licheniformis* as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 MM $MgCl_2$, 0.01% (w/v) gelatin) containing 200 μM of each dNTP, 2.5 units of AmpliTaq polymerase (Perkin-Elmer, Cetus, USA) and 100 pmol of each primer The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-μl aliquots of the amplification product was analysed by electrophoresis in 0.7% agarose gels (NuSieve, FMC). The appearance of a DNA fragment size approx. 0.8 kb indicated proper amplification of the gene segment.

Subcloning of PCR Fragment:

Fortyfive-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5. 5 μg of pMOL944 and twentyfive-μl of the purified PCR fragment was digested with PstI and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the PstI-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent *B. subtilis* PL2316. The transformed cells were plated onto LBPG-10 μg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called PL2954. The clone PL2954 was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed the DNA sequence corresponding to the mature part of the xyloglucanase in the SEQ ID NO:1 which is shown in positions 88–783.

Expression and Purification of *B. licheniformis* ylogluca-nase:

PL2954 was grown in 25×200 ml BPX media with 10 μg/ml of Kanamycin in 500 ml two baffled shakeflasks for 5 days at 37° C. at 300 rpm.

EXAMPLE 6

Cloning and Expression of the *Bacillus agaradhaerens* Xyloglucanase Gene

Genomic DNA Preparation:

Strain *Bacillus agaradhaerens*, NCIMB 40482, was propagated in liquid medium as described in WO94/01532. After 16 hours incubation at 30° C. and 300 rpm, the cells were harvested, and genomic DNA isolated by the method described by Pitcher et al. (1989)

Genomic Library Construction:

Genomic DNA was partially digested with restriction enzyme Sau3A, and size-fractionated by electrophoresis on a 0.7% agarose gel. Fragments between 2 and 7 kb in size was isolated by electrophoresis onto DEAE-cellulose paper (Dretzen, G., Bellard, M., Sassone-Corsi, P., Chambon, P. (1981) A reliable method for the recovery of DNA fragments from agarose and acrylamide gels. Anal. Biochem., 112, 295–298).

Isolated DNA fragments were ligated to BamHI digested pSJ1678 plasmid DNA, and the ligation mixture was used to transform *E. coli* SJ2.

Cells were plated on LB agar plates containing 0.1% CMC (Sodium-Carboxy-Methyl-Cellulose, Aqualon, France) and 9 μg/ml Chloramphenicol and incubated overnight at 37° C.

Identification of Positive Clones:

A DNA library in *E. coli*, constructed as described above, was screened on LB agar plates containing 0.1% CMC (Sodium-Carboxy-Methyl-Cellulose, Aqualon, France) and 9 μg/ml Chloramphenicol and incubated overnight at 37° C. The transformants were subsequently replica plated onto the same type of plates, and these new plates were incubated 8 hours or overnight at 37° C.

The original plates were coloured using 1 mg/ml of Congo Red (SIGMA, USA). The coloring was continued for half an hour with moderate orbital shaking, after which the plates were washed two times 15 minutes using 1 M NaCl.

Yellowish halos appeared at positions where cellulase positive clones were present, from the replica plates these cellulase positive clones were rescued and restreaked onto LB agar plates containing 0.1% CMC and 9 μg/ml Chloramphenicol and incubated overnight at 37° C.

One such clone (MB110) was further characterized by DNA sequencing of the cloned Sau3A DNA fragment.

The DNA was characterised by DNA sequencing by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984). The sequence encoding the mature protein, subcloned in the example below, is shown in SEQ ID NO:1. The derived protein sequence is shown in SEQ ID NO:2.

Subcloning and Expression of Xyloglucanase in *B. subtilis*:

The xyloglucanase encoding DNA sequence of the invention was PCR amplified using the PCR primer set consisting of these two oligo nucleotides:

Xyloglucanase.upper.SacII

5'-CAT TCT GCA GCC GCG GCA GAA GAT GTC ACT TCG TCA CAG-3' SEQ ID NO:13

Xyloglucanase.lower.NotI

5'-GTT GAG AAA AGC GGC CGC CAC TTC TAA AGT TCT AAA GCA CG-3' SEQ ID NO:14

Restriction sites SacII and NotI are underlined.

Chromosomal DNA isolated from *B. agaradherans* as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 μM of each dNTP, 2.5 units of AmpliTaq polymerase (Perkin-Elmer, Cetus, USA) and 100 pmol of each primer The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-μl aliquots of the amplification product was analysed by electrophoresis in 0.7% agarose gels (NuSieve, FMC). The appearance of a DNA fragment size 1.6 kb indicated proper amplification of the gene segment.

Subcloning of PCR Fragment:

Fortyfive-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5. 5 μg of pMOL944 and twentyfive-μl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 μg/ml of Kanamycin –0.1% AZCL-Xyloglucan-agar plates. After 18 hours incubation at 37° C. cells positively expressing the cloned Xyloglucanase were seen as colonies surrounded by blue halos. One such positive clone was restreaked several times on agar plates as used above, this clone was called MB563. The clone MB563 was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations.

Expression and Purification of *B. agaradhaerens* Xyloglucanase:

MB563 was grown in 25×200 ml BPX media with 10 μg/ml of Kanamycin in 500 ml two baffled shakeflasks for 5 days at 37° C. at 300 rpm.

EXAMPLE 7

Characterisation of a *Bacillus agaradhaerens* Xyloglucanase

Purification and Characterization:

7000 ml shake flask culture fluid from Bacillus with the clone MB 563 expressed as described in example 6 was received. The fermentation medium was adjusted to pH 7.5 with NaOH and flocculated using cationic flocculation agent C521 (10% solution) and 0.1% solution of anionic agent A130: To 7000 ml of fermentation medium was added 168 ml of C521 (10%) simultaneously with 335 ml of A130 under stirring at room temperature. The flocculated material was separated by centrifugation using a Sorval RC 3B centrifuge at 10,000 rpm for 30 minutes. The supernatant was clarified using Whatman glass filter number F. In total was obtained 6500 ml of clear solution containing 27,500 XGU units.

The clear solution of 2500 ml was applied to a 1000 ml Q-Sepharose column equilibrated with 50 mM Tris buffer pH 7.0. The bound enzyme was eluted using a NaCl gradient.

The partly purified product was concentrated using an Amicon ultrafiltration cell with a membrane with a cut-off value of 6 kDa. Total 70.000 XGU units and 2.5 gram of enzyme protein was obtained.

The pure sample gave a single band in SDS-PAGE with a apparent molecular weight of 61 kDa. A molar extinction coefficient of 123,040 was used for calculation of enzyme protein concentration and is based on the amino acid composition deducted from the DNA sequence.

The concentrated fraction was formulated with 40% sorbitol and used for enzyme trials in detergent and textile applications.

Immunological Methods:

Highly purified *Bacillus agaradhaerens* XEG1 obtained from clone MB 563 was used for production of antiserum.

The immunization procedure was conducted at DAKO using rabbits. Each rabbit was immunized with 100 µl cellulase (0.4 mg protein per ml) mixed with 100 µl adjuvant. Each rabbit was immunized 15 times with one weeks interval. The rabbit serum was collected and the gamma-globulin purified from the serum.

Temperature Optimum:

The AZCL xyloglucan from Megazyme was also used for determination of temperature optimum. The activity was measured at different temperatures after incubation with the *Bacillus agaradhaerens* XEG1 for 20 minutes and the release of blue colour was determined at 600 nm. The major part of the colour was released at 50° C., but still 20% relative activity was obtained at 60° C.

Steady State Kinetics on Soluble Xyloglucan and CMC:

The method for determination of activity against xyloglucan described in example 4 was applied to the *B. agaradhaerens* xyloglucanase of the invention. The substrate was diluted to at least 8 different concentrations with 4 below the apparent Km (see below).

The following apparent catalytic properties of the *Bacillus agaradhaerens* XEG1 (endo-beta-1,4-xylo-glucanases) on xyloglucan from tamarind seeds were found: At pH 7.5 the kcat of 183 per sec and a apparent Km of 0.05 gram per l was obtained. For comparison the activity on CMC (Degree of substitution 0.7 and a degree of polymerization of 200) using the same steady state kinetic method with 8 different substrate concentrations in duplicate below the Km the following data was obtained: kcat of 64 per sec and a Km of 2.2 gram per l, indicating that this enzyme prefer xyloglucan from carboxymethyl cellulose.

Alkaline activity, at pH 10 using a glycine buffer and xyloglucan substrate, resulted in a Kcat of 90 per sec and a apparent Km of 0.08 gram per l indicate that this xyloglucanase has a very high alkaline activity.

The pH activity profile using blue Megazyme AZCL xyloglucan indicate that the enzyme has more than 50% relative activity in the pH interval of 5.0 to 10.5.

In a detergent matrices using the blue Megazyme substrate the following data was obtained. In US Tide powder detergent 1 gram per l with 9 German hardness of water 66% relative activity to buffer pH 7.5. Using European conditions and powder Ariel in 5 gram per l and 18 German hardness the relative activity of 86% was obtained. These data indicate that the *Bacillus agaradhaerens* XEG1 is well suited to be used in detergent matrices.

LITERATURE

Ausubel, F. M. et al. (eds.) "Current protocols in Molecular Biology". John Wiley and Sons, 1995.

N. C. Carpita and D. M. Gibeaut (1993) The Plant Journal 3:1–30.

T. Christensen et al. Biotechnology vol 6 page 1419–1422, 1988.

Devereux et al. (1984) Nucleic Acids Res. 12, 387–395.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172:4315–4321.

Dretzen, G., Bellard, M., Sassone-Corsi, P., Chambon, P. (1981) A reliable method for the recovery of DNA fragments from agarose and acrylamide gels. Anal. Biochem., 112, 295–298.

Eriksson, O. E. & Hawksworth, D. L.: Systema Ascomycetum vol 12 (1993).

S. C. Fry et al (1992) Biochemical Journal 282:821–828

Hawksworth, D. L., Kirk, P. M., Sutton, B. C. and Pegler, D. N.: Dictionary of the fungi, International Mycological Institute, 616 pp (1995);

T. Hayashi and D. P. Delmer (1988) Carbohydrate Research 181:273–277.

Henrissat, B. 1991. A classification of glycosyl hydrolases based on amino acid sequence similaritites. Biochem. J., 280:309–316.

Henrissat, B., and A. Bairoch. 1993. New families in the classification of glycosyl hydrolases based on amino acid sequence similaritites. Biochem. J., 293:781–788.

Jülich, W.: Higher Taxa of Basidiomycetes, Bibliotheca Mycologia 85, 485 pp (1981).

Jørgensen, P. L. et al., 1990, Gene, 96, p. 37–41.

McKenzie, T. et al., 1986, Plasmid 15:93–103.

Leatherbarrow, R. J. (1992) Grafit version 3.0 Erithacus Software Ltd. Staines, U. K.

Lever, M. (1972) A new reaction for colormetric determination of carbohydrates. Anal. Biochem. 47, 273–279.

O'Donnell, K.: Zygomycetes in culture, University of Georgia, US, 257 pp (1979).

Pitcher, D. G., Saunders, N. A., Owen, R. J. (1989). Rapid extraction of bacterial genomic DNA with guanidium thiocyanate. Lett. Appl. Microbiol., 8, 151–156.

J. K. C. Rose et al (1996) Plant Physiology 110:493–499

A. L. Sonenshein, J. A. Hoch and Richard Losick (Eds.) (1993) *Bacillus subtilis* and other Gram-Positive Bacteria, American Society for microbiology, p.618.

Vincken, J. P., Beldman, G., and Voragen, A. G. J. Substrate-specificity of endoglucanases—what determines xyloglucanase activity. *Carbohydrate Research* 298(4):299–310, 1997.

Von Arx, J. A.: The genera of fungi sporulating in culture, 424 pp (1981).

R. L. Whistler and J. N. BeMiller (1993) Industrial gums: Polysaccharides and their derivatives, Academic Press Inc.

Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.

W. S. York et al (1996) Carbohydrate Research 285:99–128.

What is claimed is:

1. An isolated polypeptide exhibiting xyloglucan-specific xyloglucanase activity, wherein the polypeptide is derived from a Bacillus species and exhibits at least 50% of the xyloglucanase activity at pH 7 relative to its xyloglucanase activity at the pH optimum for its activity.

2. A polypeptide as defined in claim 1, wherein said Bacillus species is *Bacillus licheniformis*.

3. A polypeptide as defined in claim 2, wherein said *Bacillus licheniformis* is *Bacillus licheniformis* ATCC 14580.

4. A polypeptide as defined in claim 1, wherein said Bacillus species is *Bacillus agaradhaerens*.

5. A polypeptide as defined in claim 4, wherein said *Bacillus agaradhaerens* is *B. agaradhaerens*, NCIMB 40482.

6. A detergent composition comprising the polypeptide as defined in claim 1 and a surfactant.

7. A process for machine treatment of a fabric, said process comprising treating the fabric during a washing cycle of a machine washing process with a washing solution comprising a polypeptide as defined in claim 1.

8. A method for treatment of cellulosic fibres, yarn, or woven or non-woven fabric, said method comprising treating the cellulosic fibres, yarn, woven or non-woven fabric during a scouring process step with a solution comprising a polypeptide as defined in claim 1.

9. An isolated polypeptide selected from the group consisting of:

(a) a polypeptide comprising an amino acid sequence as shown in positions 1–537 of SEQ ID NO:4 and (b) a polypeptide having xyloglucan-specific xyloglucanase activity having an amino acid sequence that is at least 90% identical to amino acids 1–537 of SEQ ID NO:4 as determined by GAP provided in the GCG program package, Version 8, with a GAP creation penalty of 3.0 and a GAP extension penalty of 0.1.

10. An enzyme preparation comprising:
(i) an isolated and purified polypeptide as defined in claim 9 and
(ii) one or more enzymes selected from the group consisting of proteases, β-glucanases, hemicellulases, lipases, peroxidases, laccases, α-amylases, glucoamylases, cutinases, pectinases, reductases, oxidases, phenoloxidases, ligninases, pullulanases, pectate lyases, xylanases, pectin acetyl esterases, polygalacturonases, rhamnogalacturonases, pectin lyases, other mannanases, pectin methylesterases, cellobiohydrolases, transglutaminases; cellulases (endoglucanases) other than the polypeptide as defined in claim 9; xyloglucanases other than the polypeptide as defined in claim 9; and mixtures of any of the foregoing.

11. An isolated polypeptide selected from the group consisting of
(a) a polypeptide comprising an amino acid sequence as shown in positions 30–261 of SEQ ID NO:2 and
(b) a polypeptide having xyloglucan-specific xyloglucanase activity having an amino acid sequence that is at least 90% identical to amino acids 30–261 of SEQ ID NO:2 as determined by GAP provided in the GCG program package, Version 8, with a GAP creation penalty of 3.0 and a GAP extension penalty of 0.1.

12. An enzyme preparation comprising:
(i) an isolated and purified polypeptide according to claim 11 and
(ii) one or more enzymes selected from the group consisting of proteases, β-glucanases, hemicellulases, lipases, peroxidases, laccases, α-amylases, glucoamylases, cutinases, pectinases, reductases, oxidases, phenoloxidases, ligninases, pullulanases, pectate lyases, xylanases, pectin acetyl esterases, polygalacturonases, rhamnogalacturonases, pectin lyases, other mannanases, pectin methylesterases, cellobiohydrolases, transglutaminases; cellulases (endoglucanases) other than the polypeptide as defined in claim 9; xyloglucanases other than the polypeptide as defined in claim 9; and mixtures of any of the foregoing.

* * * * *